US007285665B2

(12) United States Patent
Cantrell et al.

(10) Patent No.: US 7,285,665 B2
(45) Date of Patent: Oct. 23, 2007

(54) PROCESS FOR THE PREPARATION OF QUATERNARY N-ALKYL MORPHINAN ALKALOID SALTS

(75) Inventors: Gary L. Cantrell, Troy, IL (US); Robert E. Halvachs, Belleville, IL (US)

(73) Assignee: Mallinckrodt Inc., St. Louis, MO (US)

( * ) Notice: Subject to any disclaimer, the term of this patent is extended or adjusted under 35 U.S.C. 154(b) by 168 days.

(21) Appl. No.: 10/530,446

(22) PCT Filed: Nov. 5, 2003

(86) PCT No.: PCT/US03/35463

§ 371 (c)(1),
(2), (4) Date: Apr. 5, 2005

(87) PCT Pub. No.: WO2004/043964

PCT Pub. Date: May 27, 2004

(65) Prior Publication Data
US 2006/0014771 A1 Jan. 19, 2006

(51) Int. Cl.
C07D 489/02 (2006.01)
C07D 489/08 (2006.01)
(52) U.S. Cl. .............................. 546/44; 546/45; 546/46
(58) Field of Classification Search .................. 546/44, 546/45, 46
See application file for complete search history.

(56) References Cited

U.S. PATENT DOCUMENTS

| 3,101,339 | A | 8/1963 | Zeile et al. |
| 4,141,897 | A | 2/1979 | Olofson et al. |
| 4,176,186 | A | 11/1979 | Goldberg et al. |
| 4,322,426 | A | 3/1982 | Hermann et al. |
| 4,535,157 | A | 8/1985 | Meltzer et al. |
| 5,240,933 | A | 8/1993 | Merz et al. |
| 5,352,680 | A | 10/1994 | Portoghese et al. |
| 5,574,159 | A | 11/1996 | Chang et al. |
| 5,668,285 | A | 9/1997 | Rice et al. |
| 5,869,669 | A | 2/1999 | Huang et al. |
| 5,907,069 | A | 5/1999 | Becnel et al. |
| 5,922,876 | A | 7/1999 | Huang et al. |
| 5,948,788 | A | 9/1999 | Huang et al. |
| 5,952,495 | A | 9/1999 | Huang et al. |
| 5,981,474 | A | 11/1999 | Manning et al. |
| 6,008,354 | A | 12/1999 | Huang et al. |
| 6,008,355 | A | 12/1999 | Huang et al. |
| 6,013,796 | A | 1/2000 | Huang et al. |
| 6,365,742 | B1 | 4/2002 | Mudryk et al. |
| 2005/0182258 | A1 | 8/2005 | Schmidhammer et al. |

FOREIGN PATENT DOCUMENTS

| PL | 124 001 | 7/1985 |
| WO | WO95/31463 A1 | 11/1995 |
| WO | WO 2004/005294 A2 | 1/2004 |

OTHER PUBLICATIONS

Bognár, R., et al., "Selective Quaternization in the Morphine Series," Tetrahedron Letters, 1964, pp. 2867-2871, No. 39.
International Search Report for PCT/US03/35463 dated Jul. 1, 2004, 3 pages.
Iorio, M.A., et al., "Diastereoisomeric Quaternary Morphinium Salts: Synthesis, Stereochemistry and Analgesic Properties," European Journal of Medicinal Chemistry, 1984, pp. 11-16, vol. 19, No. 1.
Manoharan, T.S., et al., "Convenient Method for Replacement of Tertiary N-Methyl by Other Alkyl Groups: Application to Morphine Alkaloids," Indian Journal of Chemistry, Jan. 1984, pp. 5-11, vol. 23B.
Musich et al., Reaction of O-methyl-N, $N^1$-Diisopropylisourea with Amino Acids and Amines, Journal of Organic Chemistry (1977), 42(1), pp. 139-141.
Giger et al., Synthesis and Reactions of the diels-Alder Adduct of Thebaine with 4-phenyl-1,2,4-triazoline-3,5-dione, Tetrahedron (1973), 29(16), pp. 2387-2391.
Koczka et al., Selective Quaternization of Compounds with Morphine Skeleton, Acta. Chim. Acad. Sci. Hung. (1967), 51(4), pp. 393-402.
Seki, Isao, Studies on the Morphine Alkaloids and its Related Compounds. XIV. Preparation of 6-Amino-hydrophenanthrene Compounds from Hofmann Degradation Products of the Morphine Alkaloids, Chemical & Pharmaceutical Bulletin (1966), 14(5), pp. 453-461.
Fry et al., Mannich Derivatives of Analgesic Agents, Journal of Organic Chemistry (1959), 24, pp. 116-117.
Bentley et al., The Reduction of Thebaine and Dihydrothebaine by Sodium and Ammonia, Journal of the Chemical Society, Abstracts (1952), pp. 958-966.
Schultz et al., Thebaine Cyclopropanation, Russian Journal of Organic chemistry (Translation of Zhurnal Organicheskoi Khimii) (2003), 39(8), pp. 1083-1088.
Otto et al., Selection and Amplification of Hosts from Dynamic combinatorial Libraries of Macrocyclic Disulfides, Science (Washington, DC, United States) (2002), 297(5581), pp. 590-593 & Supporting Online Material.
Lopez et al., Photoxidation of Thebaine. A Route to 14-Hydroxymorphinones and Hydrodibenzofuran Analogs of Methadone, Tetrahedron Letters (1994), 35(31), pp. 5727-5730.
Manoharan et al., Stereoselectivity in Quaternization of Thebaine: 270 MHz PMR Spectroscopic Studies, Indian Journal of Chemistry, Section B: Organic Chemistry Including Medicinal chemistry (1987), 26B(2), pp. 140-142.
Shults et al., Tranformations of Quaternary Tetrahydrothebaine Sulfones, Zh. Org. Khim. (1993), 29(6), pp. 1149-1162, (English pp. 953-963).
Funke et al., $A^1H$ and $^{13}C$ Nuclear Magnetic Resonance Study of Three Quaternary Salts of Naloxone and Oxymorphone, J. Chem. Soc. Perkin Trans. (1986) 2, pp. 735-738.
Lopez et al., The [4+2] Addition of Singlet Oxygen to Thebaine: New Access to Highly Functionalized Morphine Derivatives via Opioid Endoperoxides, J. Org. Chem. (2000), 65(15), pp. 4671-4678.

Primary Examiner—Charanjit S. Aulakh
(74) Attorney, Agent, or Firm—Senniger Powers

(57) ABSTRACT

A process for the preparation of a quaternary derivative of the morphinan alkaloid, the process comprising contacting a tertiary N-substituted morphinan alkaloid with an alkyl halide in an anhydrous solvent system, wherein the solvent system comprises an aprotic dipolar solvent with the aprotic dipolar solvent constituting at least 25 wt % of the solvent system.

50 Claims, No Drawings

PROCESS FOR THE PREPARATION OF QUATERNARY N-ALKYL MORPHINAN ALKALOID SALTS

BACKGROUND OF THE INVENTION

The present invention generally relates to a process for the synthesis and/or recovery of quaternary N-alkyl salts of morphinan alkaloids.

N-methyl quaternary derivatives of morphinan alkaloids such as naltrexone ((5α)-17-(cyclopropylmethyl)-4,5-epoxy-3,14-dihydroxymorphinan-6-one sometimes referred to as N-cyclopropylmethyl-noroxymorphone) and naloxone ((5α)-4,5-epoxy-3,14-dihydroxy-17-(2-propenyl)morphinan-6-one sometimes referred to as N-allyl-noroxymorphone) have useful pharmacological properties as potent antagonists of the mu receptor. They bind to peripheral receptors primarily located in the gastrointestinal tract, act as antagonists and effectively mitigate some of the undesirable side effects of opiate therapy such as constipation and nausea. Because of their ionic charge, however, they do not traverse the blood brain barrier into the central nervous system; hence, the central activity of opiates responsible for pain relief is not blocked in the presence of these quaternary derivatives.

In U.S. Pat. No. 4,176,186. Goldberg, et al. generally describe the preparation of quaternary derivatives of certain morphinan alkaloids by quaternizing a tertiary N-substituted morphinan alkaloid with a methylating agent such as methyl bromide, methyl iodide or dimethylsulfate. Goldberg et al. disclose that the methylating agent itself may be used as the solvent or, alternatively, another solvent medium such as methanol, ethanol, or other alcohols, methylene chloride, chloroform, tetrahydrofuran, dioxane, dimethylformamide, dimethylsulfoxide, acetonitrile, nitromethane or hexamethylphosphoric triamide may be used. Goldberg et al. state that they especially prefer acetone and, in their Example 5, they dissolve N-cyclopropylmethylnoroxy-morphone in a mixture consisting of 50 ml of absolute acetone and 0.5 ml of dimethylformamide and then admix the resulting solution with methyl bromide. Methyl bromide was used in excess, greater than six-fold molar excess relative to the free base, over a period of 3 weeks in a pressure vessel.

SUMMARY OF THE INVENTION

Among the various aspects of the present invention is an improved process for the preparation and/or recovery of quaternary morphinan alkaloids.

Briefly, therefore, the present invention is a process for the preparation of a quaternary derivative of the morphinan alkaloid. The process comprises contacting a tertiary N-substituted morphinan alkaloid with an alkyl halide in an anhydrous solvent system, wherein the solvent system comprises an aprotic dipolar solvent with the aprotic dipolar solvent constituting at least 25 wt % of the solvent system.

The present invention is further directed to a process for separating a liquid mixture containing a 3-alkoxymorphinan alkaloid and a 3-hydroxymorphinan alkaloid. The process comprises contacting the mixture with a strong base, thereby converting the 3-hydroxy morphinan alkaloid to a salt, precipitating the salt but not the 3-alkoxymorphinan alkaloid from the liquid, and separating the salt precipitate from the 3-alkoxymorphinan alkaloid.

Other objects and features of this invention will be in part apparent and in part pointed out hereinafter.

DETAILED DESCRIPTION OF THE PREFERRED EMBODIMENTS

Among the various aspects of the present invention is a process for the N-alkylation of ternary morphinan alkaloid bases. The product of the N-alkylation is a quaternary morphinan alkaloid derivative.

In one embodiment, the ternary morphinan alkaloid base is represented by Formula 1 and the product is represented by Formula 1A:

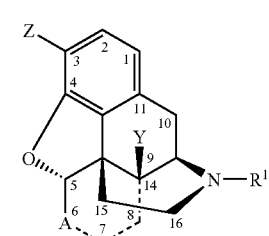

Formula 1

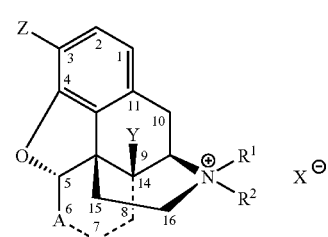

Formula 1A wherein

A is —C(O)—, —C(S)—, —C(=CH$_2$)—, —CH(A$_1$)—, or —C(A$_1$)=,

A$_1$ is hydroxy, alkoxy, or acyloxy,

R$^1$ is hydrocarbyl or substituted hydrocarbyl,

R$^2$ is hydrocarbyl or substituted hydrocarbyl,

X$^\ominus$ is an anion,

Y, if present, is hydrogen, hydroxy, alkoxy, or acyloxy,

Z is hydroxy, alkoxy, or acyloxy, and the dashed lines between the carbon atoms at positions 6 and 7, 7 and 8, and 8 and 14, respectively, represent (i) carbon-carbon single bonds, (ii) carbon-carbon single bonds between positions 6 and 7 and between positions 8 and 14, and a double bond between positions 7 and 8, or (iii) conjugated carbon-carbon double bonds between positions 6 and 7 and positions 8 and 14, with the proviso that Y is not present if there is a double bond between the carbons at positions 8 and 14.

In one embodiment, the ternary morphinan alkaloid base is represented by Formula 2 and the product is represented by Formula 2A:

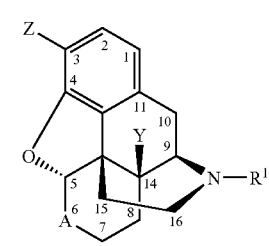

Formula 2

Formula 2A

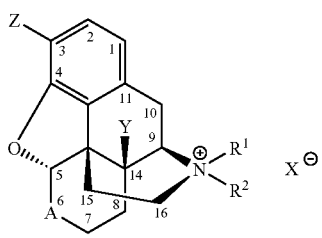

wherein
A is —C(O)—, —C(S)—, —C(=CH$_2$)—, or —CH(A$_1$)—,
A$_1$ is hydroxy, alkoxy, or acyloxy,
R$^1$ is hydrocarbyl or substituted hydrocarbyl,
R$^2$ is hydrocarbyl or substituted hydrocarbyl,
X$^\ominus$ is an anion,
Y is hydrogen, hydroxy, alkoxy, or acyloxy, and
Z is hydroxy, alkoxy, or acyloxy Representative ternary morphinan alkaloids falling within the scope of Formula 2 include naltrexone ((5α)-17-(cyclopropylmethyl)-4,5-epoxy-3,14-dihydroxymorphinan-6-one), oxymorphone ((5α)-4,5-epoxy-3,14-dihydroxy-17-methylmorphinan-6-one), oxycodone ((5α)-4,5-epoxy-14-hydroxy-3-methoxy-17-methylmorphinan-6-one), hydromorphone ((5α)-4,5-epoxy-3-hydroxy-17-methylmorphinan-6-one), naloxone ((5α)-4,5-epoxy-3,14-dihydroxy-17-(2-propenyl)morphinan-6-one), nalmefene ((5α)-17-(cyclopropylmethyl)-4,5-epoxy-6-methylenemorphinan-3,14-diol) and nalbuphine ((5α)-17-(cyclobutylmethyl)-4,5-epoxymorphinan-3,6,14-triol). Preferred ternary morphinan alkaloids and quaternary derivatives thereof falling within the scope of Formulae 2 and 2A correspond to Formulae 2" and 2"':

Formula 2'

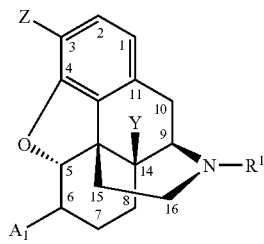

Formula 2A'

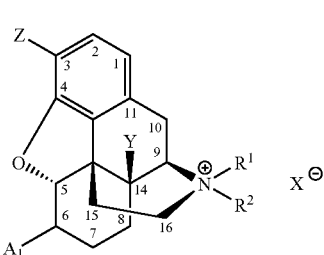

wherein R$^1$, R$^2$, X$^\ominus$, Y and Z are as defined in connection with Formulae 2 and 2A and A$_{10}$ is oxygen, sulfur or methylene; in one embodiment, A$_{10}$ is preferably oxygen or methylene. Ternary morphinan alkaloids falling within the scope of Formula 2' include naltrexone, oxymorphone, oxycodone, hydromorphone, naloxone, and nalmefene. Other preferred ternary morphinan alkaloids and quaternary derivatives thereof falling within the scope of Formulae 2 and 2A correspond to Formulae 2" and 2A":

Formula 2"

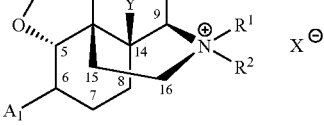

Formula 2A"

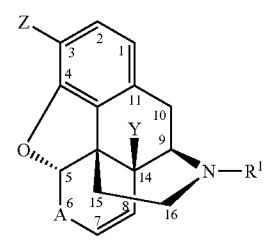

wherein R$^1$, R$^2$, X$^\ominus$, Y and Z are as defined in connection with Formulae 2 and 2A and A$_1$ is hydroxy, alkoxy or acyloxy. Ternary morphinan alkaloids and falling within the scope of Formulae 2" include nalbuphine.

In one embodiment, the ternary morphinan alkaloid base is represented by Formula 3 and the product is represented by Formula 3A:

Formula 3

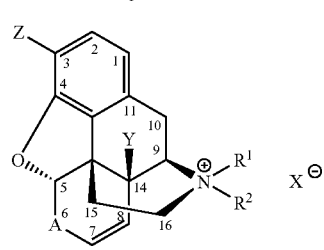

Formula 3A wherein
A is —C(O)—, —C(S)—, —C(=CH$_2$)—, or —CH(A$_1$)—,
A$_1$ is hydroxy, alkoxy, or acyloxy,
R$^1$ is hydrocarbyl or substituted hydrocarbyl,
R$^2$ is hydrocarbyl or substituted hydrocarbyl,
X$^\ominus$ is an anion,
Y is hydrogen, hydroxy, alkoxy, or acyloxy, and
Z is hydroxy, alkoxy, or acyloxy.

Representative ternary morphinan alkaloids falling within the scope of Formula 3 include morphine ((5α,6α)-7,8- didehydro-4,5-epoxy-17-methylmorphinan-3,6-diol), codeine ((5α,6α)-7,8-didehydro-4,5-epoxy-3-methoxy-17-methylmorphinan-6-ol), codeinone ((5α)-7,8-didehydro-4,5-epoxy-3-methoxy-17-methylmorphinan-6-one) and 14-hydroxy-codeinone ((5α)-7,8-didehydro-4,5-epoxy-14-hydroxy-3-methoxy-17-methylmorphinan-6-one).

In another embodiment, the ternary morphinan alkaloid base is represented by Formula 4 and the product is represented by Formula 4A:

Formula 4

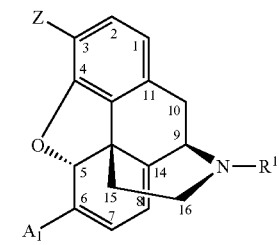

Formula 4A

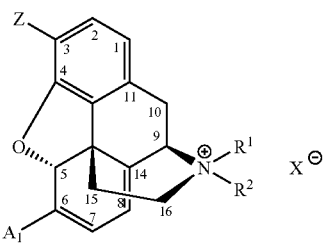

wherein $A_1$ is hydroxy, alkoxy, or acyloxy, $R^1$ is hydrocarbyl or substituted hydrocarbyl, $R^2$ is hydrocarbyl or substituted hydrocarbyl, $X^\ominus$ is an anion, and Z is hydroxy, alkoxy, or acyloxy.

Representative ternary morphinan alkaloids and quaternary derivatives thereof falling within the scope of Formula 4 include thebaine ((5α)-6,7,8,14-tetradehydro-4,5-epoxy-3,6-dimethoxy-17-methylmorphinan).

In each of these embodiments in which a ternary alkaloid base is alkylated to form the corresponding N-alkyl quaternary alkaloid salt represented by Formula 1A, 2A, 2A', 2A", 3A, or 4A, Z is preferably hydroxy, alkoxy or acyloxy, more preferably hydroxy or methoxy. For example, in each of these embodiments Z may be selected from —OCH$_3$, —OAc, —OTHP, —OSiR$_3$ (wherein each R is independently hydrocarbyl, preferably lower alkyl), —OBn, —OBz, —OBs, —OTs, or —OMs. In each of these embodiments, Y, if present, is preferably hydrogen, hydroxy, alkoxy or acyloxy, more preferably hydrogen or hydroxy. For example, in each of these embodiments Y, if present, may be selected from —OCH$_3$, —OAc, —OTHP, —OSiR (wherein each R is independently hydrocarbyl, preferably lower alkyl), —OBn, —OBz, —OBs, —OTs, and —OMs. In each of these embodiments, $R^1$ is preferably methyl, ethyl, propyl, allyl (—CH$_2$CH=CH$_2$), chloroallyl, cyclopropylmethyl, cyclobutylmethyl, or propargyl. In each of these embodiments, $R^2$ is preferably alkyl, alkenyl or alkaryl, more preferably lower alkyl, and typically methyl. In each of these embodiments, $X^\ominus$ is preferably a halide or an anion such as iodide, chloride, nitrate, sulfate, or phosphate for the halide anion. If $X^\ominus$ is a halide, it is preferably bromide.

In general, the N-alkyl quaternary derivative of the ternary alkaloid base is prepared by contacting the base with an alkyl halide in an anhydrous solvent system. Relatively concentrated solutions are preferred. That is, the reaction mixture preferably comprises no more than about 2 equivalents of solvent for each equivalent of ternary alkaloid base to solvent. In some embodiments, the reaction mixture comprises no more than about 1.75 equivalents of solvent for each equivalent of ternary alkaloid base. In other embodiments, the reaction mixture comprises no more than about 1.5 equivalents of solvent for each equivalent of ternary alkaloid base.

A range of alkylating agents may be used in the process of the present invention. In general, alkylating agents comprising 1 to 8 carbons, optionally substituted and optionally unsaturated are preferred. Thus, for example, the alkylating agent may be a methyl, ethyl, propyl, allyl, cyclopropyl, or benzyl halide. While alkyl chlorides and alkyl iodides may be used, it is generally preferred that the alkyl halide be an alkyl bromide. Relative to the corresponding alkyl bromides, under certain conditions alkylations with alkyl chlorides tend to proceed slowly and alkyl iodides tend to lead to over alkylation of the ternary alkaloid substrates. In one embodiment, for example, the alkylating agent is methyl, ethyl, propyl, allyl, cyclopropyl or benzyl bromide. Preferably, it is methyl bromide.

The solvent system for the N-alkylation comprises an aprotic, dipolar solvent and is anhydrous. That is, the solvent system comprises less than about 0.5 wt. % water, typically less than about 0.2 wt. % water, still more typically less than 0.1 wt. % water, and in some embodiments, less than 0.05 wt. % water. In addition, it is preferred that the aprotic, dipolar solvent constitute a significant fraction of the solvent system; for example, in one embodiment the aprotic, dipolar solvent constitutes at least about 25 wt % of the solvent system. In another embodiment, the aprotic, dipolar solvent constitutes at least about 50 wt % of the solvent system. In a further embodiment, the aprotic, dipolar solvent constitutes at least about 75 wt % of the solvent system. In a further embodiment, the aprotic, dipolar solvent constitutes at least about 90 wt % of the solvent system. Exemplary aprotic dipolar solvents include dimethyl acetamide, dimethyl formamide, N-methylpyrrolidinone, acetonitrile, hexamethylphosphor-amide ("HMPA"), and mixtures thereof. N-methylpyrrolidinone (1-methyl-2-pyrrolidinone) is typically preferred, either alone or in combination with another aprotic, dipolar solvent. In addition to the aprotic dipolar solvent (or mixture of aprotic dipolar solvents), the solvent system may additionally comprise other solvents such as acetone, ether, hydrocarbon, toluene, benzene, and halobenzene.

The reaction may be carried out over a wide range of temperatures and pressures. Surprisingly, however, it has been discovered that when methyl bromide gas is dissolved in anhydrous 1-methyl-2-pyrrolidinone, the methyl bromide is predominantly retained at temperatures of 85° C. at relatively modest elevated pressures (e.g., ≦2 atmosphere, ≦1.5 atmospheres, ≦1.25 atmospheres) or even at atmospheric pressures without the use of relatively expensive pressure vessels. In such embodiments, the reaction will be carried out at a temperature somewhere in the range of room temperature (about 25° C.) to about 90° C., typically about 55 to about 85° C. Advantageously, the rate, conversion, yield and concentration of naltrexone base to the N-methylated product in anhydrous 1-methyl-2-pyrrolidinone is dramatically increased at lower reaction temperatures (<70° C.)

as compared to the reaction in acetone carried out at 125-140° C. (>10 atm) over 24 hours.

The product is obtained after completion of reaction by cooling the reaction to room temperature. In one embodiment, an aprotic solvent of lower polarity in which the product is not soluble is added to the reaction mixture to increase "flowability" and to enhance precipitation. The resulting mixture is preferably stirred, vacuum filtered and dried to yield a crude product. In a preferred embodiment, the aprotic solvent of low polarity used is selected from acetone, ether, or hydrocarbon such as benzene or toluene.

In general and regardless of synthetic route, N-alkylations of morphinan substrates that contain a 3-hydroxy moiety may yield undesirable 3-alkoxymorphinans. Crude product mixtures containing 3-hydroxy and 3-alkoxymorphinans may be purified by adding strong base, e.g., sodium methoxide, NaOH, or KOH in methanol/water, heating the mixture to convert the 3-hydroxymorphinan to its salt (e.g., sodium salt), adding additional methanol, cooling to precipitate the salt, filtering and drying. Advantageously, the 3-alkoxymorphinan remains in solution and does not precipitate along with the salt; as a result, the salt and the 3-alkoxymorphinan may be readily separated.

The desired N-alkyl morphinan may be regenerated from the salt by redissolving the salt (for example, in a methanol/water solution), adjusting the solution to a low pH (for example, a pH of 0.5 to 1 using 45% hydrobromic acid) to regenerate a hydroxy group at the 3-position, and precipitating the product. In a preferred embodiment, the precipitated product is recovered by vacuum filtration, washing with additional methanol and drying to 75° C.

When the alkylating agent is an alkyl halide, the N-alkyl morphinan alkaloid will contain a halide anion. This anion may be exchanged at various stages in the process by treating the N-alkyl morphinan alkaloid with a protic acid, thereby exchanging an anion such as iodide, chloride, nitrate, sulfate, or phosphate for the halide anion.

As described in greater details in the Examples, purification of crude product from the synthesis described above is capable of yielding N-alkyl product of 99.5% purity by HPLC relative to an analytical standard.

DEFINITIONS

As used herein, "Ac" means acetyl, "Bn" means benzyl, "Bs" means brosyl, "Bz" means benzoyl, "Ms" means mesyl, "THP" means tetrahydropyranyl, and "Ts" means tosyl.

The term anhydrous solvent as used herein refers to solvents containing less than 0.5% by weight water, preferably maintained and handled under nitrogen gas during a reaction.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, hetero- cyclo, alkoxy, alkenoxy, alkynoxy, aryloxy, hydroxy, keto, acyl, acyloxy, nitro, tertiaryamino, amido, nitro, cyano, ketals, acetals, esters and ethers.

Unless otherwise indicated, the alkyl groups described herein are preferably lower alkyl containing from one to eight carbon atoms in the principal chain. They may be straight or branched chain or cyclic and include methyl, ethyl, propyl, isopropyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include allyl, benzyl, ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "acyl," as used herein alone or as part of another group, denotes the moiety formed by removal of the hydroxyl group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "halide" refers to fluoride, chloride, bromide, or iodide ions.

The term "narcotics" as used herein refers to drugs that depress the central nervous system and relieve pain when used in moderate doses . . .

The term "opioid" as used herein refers to non-opium-derived (synthetic or naturally occuring) narcotics that act on the central nervous system to decrease the sensation of pain.

The following examples illustrate the invention.

EXAMPLE 1

Synthesis of
N-Cyclopropylmethyl-Noroxymorphone
MethoBromide Bromomethane in
1-methyl-2-pyrrolidinone A 3-necked 500-mL flask was fitted with an addition funnel, thermocouple, condenser and a mechanical stirrer. 100 mL of 1-methyl-2-pyrrolidinone was added to the flask under a sweep of dry nitrogen and was heated to 55° C. The addition funnel was replaced with a powder funnel, 100 gm of naltrexone anhydrous base was added with stirring, the funnel was "washed down" with 25 mL of 1-methyl-2- pyrrolidinone and the temperature was adjusted to 55-58° C. The addition funnel was placed back on the 3-necked flask. Separately, 25 mL of anhydrous 1-methyl-2-pyrrolidinone was cooled in a graduated cylinder. Methyl bromide gas was condensed in a lecture bottle using an ice bath and 25 mL was measured out as a liquid into another cold graduated cylinder. The cold methyl bromide liquid and 1-methyl-2-pyrrolidinone were combined and mixed. The methyl bromide solution was poured into the addition funnel and then added dropwise to the naltrexone base under a slow sweep of dry nitrogen. The reaction temperature was increased to 61-65° C. A mild exotherm was noted.

After about one hour, a fine white suspension of N-naltrexone methyl bromide could be observed which increased throughout the 8 hour reaction time. The mixture was then cooled to 20-55° C. Acetone was poured into the suspension to facilitate the precipitation of soluble product. The slurry was cooled to ice bath temperature and stirred for 1 to 2 hours. The product was recovered by vacuum filtration and washed with 75 mL of additional acetone. The product was dried in a convection oven to a constant weight. The crude weight yield was 80 to 85 g with a HPLC assay of 90-93% area % purity.

EXAMPLE 2

Purification Procedure for Products from
N-alkylations
N-Cyclopropylmethyl-Noroxymorphone
MethoBromide The undesirable phenolic (O-alkyl) side-products were removed by first converting the O-alkyl impurity in crude N-naltrexone methyl bromide into its sodium alkoxide salt utilizing a strong base, e.g., 40 mL of 25% sodium methoxide in methanol/water (220 mL/120 mL). The solution was heated to 50-65° C. with an additional 500 mL of methanol. The solution was cooled to 20-25° C. for 60-90 min. The sodium salt crystallized on stirring and was recovered by vacuum filtration. After drying at 60° C. under nitrogen, the sodium salt weighed 53-55 g.

The product was regenerated by adjusting the pH of a methanol/water (100 mL, ratio 5:7.5) sodium salt solution to 0.5-1 with 25 g of 45% hydrobromic acid. The solution was filtered, 150 mL of methanol added, the temperature was adjusted to 50-55° C. and finally cooled to ice-bath temperature. The white precipitated product was recovered by vacuum filtration and washed with 75 mL of methanol. After drying to 75° C., the purified product weighed ~45 g. The product was 99.5% pure by HPLC assessment relative to an analytical standard.

The procedure described above is applicable to other N-alkylations.

EXAMPLE 3

Synthesis of
N-Cyclopropylmethyl-Noroxymorphone
MethoBromide Bromomethane in
N,N-dimethylformamide (DMF)

Naltrexone base (40.0 grams) was dissolved in N,N-dimethylformamide (DMF) (50 mL Mallinckrodt, AR) with mild heating and then purged with dry house nitrogen. Methyl bromide (5 mL, Aldrich) cooled to ice bath temperature was measured out into a cold (~5° C.) 10 mL graduated cylinder and quickly added to the reaction flask. With the bubbler left in place, the glass flask was heated to 65° C. for ten hours. The crude product was recovered from the DMF by precipitation with acetone (75 mL, Mallinckrodt AR) after a short reflux period. A white solid was isolated by vacuum filtration and washed with acetone (Mallinckrodt AR). The crude product (22.7 g) was dissolved in methanol (Mallinckrodt AR)/deionized water (110 mL, 80/20), charcoal-treated (0.5 g, DARCO KB-B, Ba# M-1014) and then allowed to crystallize. The salt like product (17.2 g) was recrystallized again from methanol/deionized water (90 mL). The product, naltrexone methobromide, weighed 12.3 grams after drying in a vacuum oven overnight. HPLC analysis indicated that no O-methylated products were left. The starting base was the only remaining impurity at a concentration of 0.64 wt./wt. The product assayed at 99.36 wt./wt. %.

EXAMPLE 4

Synthesis of
N-Cyclopropylmethyl-Noroxymorphone
MethoBromide Bromomethane in
1-Methyl-2-Pyrrolidinone (NMP)

To a 3-necked 250 mL flask fitted with a thermocouple, addition funnel, condenser and a mechanical stirrer, was added 50 mL of fresh anhydrous 1-methyl-2-pyrrolidinone (Aldrich) under a sweep of dry nitrogen. The solution was heated to 55° C. The addition funnel was replaced with a powder funnel and anhydrous naltrexone base (39.5 grams) was added with stirring. After the funnel was "washed down" with 10 mL of additional 1-methyl-2-pyrrolidinone, the temperature was adjusted to 55-58° C. The addition funnel was placed on the flask. Separately, 10 mL of anhydrous 1-methyl-2-pyrrolidinone was cooled in a graduated cylinder. Methyl bromide gas was condensed in a lecture bottle using an ice bath and 10 mL was measured out as a liquid into another cold graduated cylinder. The cold methyl bromide liquid and 1-methyl-2-pyrrolidinone were combined and mixed. The methyl bromide solution was poured into the addition funnel and then added dropwise to the naltrexone base under a slow sweep of dry nitrogen. An exotherm was noted and the temperature of the solution climbed to 66° C. The reaction temperature and time was set at 62.5° C. for nine hours. After an hour, a fine white suspension of naltrexone methobromide began to form. At the end of nine hours the heating was discontinued and the mixture was allowed to cool to room temperature and left stirring overnight. Acetone (75 mL) was poured into the suspension to facilitate the precipitation of soluble product. The slurry was cooled to ice bath temperature and stirred. The product was recovered by vacuum filtration and washed with 25 mL of additional acetone. The product was dried to a constant weight in a vacuum oven set at 60° C. The yield of the unpurified product was 31.8 g.

EXAMPLE 5

Synthesis of
N-Cyclopropylmethyl-Noroxymorphone
MethoBromide Reduced Bromomethane in
1-Methyl-2-Pyrrolidinone (NMP) Ambient Pressure To a 3-necked 250 mL flask fitted with a thermocouple, addition funnel, condenser and a mechanical stirrer, was added 50 mL of 1-methyl-2-pyrrolidinone under a sweep of dry nitrogen. The solution was heated to 55° C. The addition funnel was replaced with a powder funnel and anhydrous naltrexone base (40 grams) was added with stirring. After the funnel was "washed down" with 10 mL of 1-methyl-2-pyrrolidinone, the temperature was adjusted to 55-58° C. The addition funnel was placed on the flask. Separately, 10 mL of anhydrous 1-methyl-2-pyrrolidinone was cooled in a graduated cylinder. Methyl bromide gas was condensed in a lecture bottle using an ice bath and 8 mL was measured out as a liquid into another cold graduated cylinder. The cold methyl bromide liquid and 1-methyl-2-pyrrolidinone were combined and mixed. The methyl bromide solution was poured into the addition funnel and then added dropwise to the naltrexone base under a slow sweep of dry nitrogen. The reaction temperature was increased to a set temperature of 62.5° C. for nine hours. After about two hours, a fine white suspension of naltrexone methobromide began to form. At the end of nine hours the heating was discontinued and the mixture was allowed to cool to room temperature and left stirring overnight. Acetone (75 mL) was poured into the suspension to facilitate the precipitation of soluble product. The slurry was cooled to ice bath temperature and stirred. The product was recovered by vacuum filtration and washed with 25 mL of additional acetone. The product was dried to a constant weight in a vacuum oven set at 60° C. The yield of the unpurified product was 26.9 g.

EXAMPLE 6

Synthesis of
N-Cyclopropylmethyl-Noroxymorphone
MethoBromide Bromomethane in NMP at 72.5° C.
for Six Hours To a 25 mL flask fitted with a condenser and stirring bar was added 3 mL of fresh anhydrous 1-methyl-2-pyrrolidinone (Aldrich) under a sweep of dry nitrogen. Anhydrous naltrexone base (2.0 grams) was added with stirring. Methyl bromide gas was condensed in a lecture bottle using an ice bath and 0.5 mL was measured out as a liquid into another cold graduated cylinder. The methyl bromide was poured into the naltrexone base suspension under a slow sweep of dry nitrogen. The reaction temperature and time was set at 72.5° C. for six hours. At the end of six hours, the heating was discontinued and the mixture was allowed to cool to room temperature and left stirring overnight. Acetone (15 mL) was poured into the suspension to facilitate the precipitation of soluble product. The slurry was cooled to ice bath temperature and stirred. The product was recovered by vacuum filtration and washed with additional acetone. The product was dried to a constant weight in a vacuum oven set at 60° C. The yield of the unpurified product was 1.77 g.

EXAMPLE 7

Synthesis of
N-Cyclopropylmethyl-Noroxymorphone
MethoBromide Bromomethane in NMP at 57.5° C.
for Twelve Hours To a 25 mL flask fitted with a condenser and stirring bar was added 3 mL of fresh anhydrous 1-methyl-2-pyrrolidinone (Aldrich) under a sweep of dry nitrogen. Anhydrous naltrexone base (2.0 grams) was added with stirring. Methyl bromide gas was condensed in a lecture bottle using an ice bath and 0.5 mL was measured out as a liquid into another cold graduated cylinder. The methyl bromide was poured into the naltrexone base suspension under a slow sweep of dry nitrogen. The reaction temperature and time was set at 57.5° C. for twelve hours. At the end of this time, the heating was discontinued and the mixture was allowed to cool to room temperature and left stirring overnight. Acetone (15 mL) was poured into the suspension to facilitate the precipitation of soluble product. The slurry was cooled to ice bath temperature and stirred. The product was recovered by vacuum filtration and washed with additional acetone. The product was dried to a constant weight in a vacuum oven set at 60° C. The yield of the unpurified product was 1.87 g.

EXAMPLE 8

Synthesis of
N-Cyclopropylmethyl-Noroxymorphone
MethoBromide Bromomethane in NMP at 60° C.
for Twelve Hours To a 25 mL flask fitted with a condenser connected to a bubbler and stirring bar was added 3 mL of fresh anhydrous 1-methyl-2-pyrrolidinone (Aldrich) under a sweep of dry nitrogen. Anhydrous naltrexone base (2.06 grams) was added with stirring. Methyl bromide gas was condensed in a lecture bottle using an ice bath and 0.5 mL was measured out as a liquid into another cold graduated cylinder. The methyl bromide was poured into the naltrexone base suspension under a slow sweep of dry nitrogen. The reaction temperature and time was set at 60° C. for twelve hours. At the end of this time, the heating was discontinued and the mixture was allowed to cool to room temperature and then left stirring overnight. Acetone (15 mL) was poured into the suspension to facilitate the precipitation of soluble product. The slurry was cooled to ice bath temperature and stirred. The product was recovered by vacuum filtration and washed with additional acetone. The product was dried one hour in a vacuum oven at 60° C. The yield of the unpurified product was 1.84 g.

EXAMPLE 9

Synthesis of
N-Cyclopropylmethyl-Noroxymorphone
MethoBromide Bromomethane in NMP at 65° C.
for Eight Hours To a 25 mL flask fitted with a condenser and stirring bar was added 5 mL of fresh anhydrous 1-methyl-2-pyrrolidinone (Aldrich) under a sweep of dry nitrogen. Anhydrous naltrexone base (4.08 grams) was added with stirring. Methyl bromide gas was condensed in a lecture bottle using an ice bath and 1 mL was measured out as a liquid into another cold graduated cylinder. The methyl bromide was poured Into the naltrexone base suspension under a slow sweep of dry nitrogen. The reaction temperature and time was set at 65° C. for eight hours. A white suspension began to form after one hour. At the end of eight hours, the heating was discontinued and the mixture was allowed to cool to room temperature and left stirring overnight. Acetone (15 mL) was poured into the suspension to facilitate the precipitation of soluble product. The slurry was cooled to ice bath temperature and stirred. The product was recovered by vacuum filtration and washed with additional acetone. The product was dried to a constant weight in a vacuum oven set at 60° C. The yield of the unpurified product was 3.9 g's at a 93.5% purity by area on HPLC analysis. 3.68 Grams of white salt was obtained after recrystallization from methanol/water and drying.

EXAMPLE 10

Synthesis of N-Cyclopropylmethyl-Noroxymorphone MethoBromide Bromomethane in N,N-Dimethylacetamide (DMAC)

To a 25 mL flask fitted with a condenser and stirring bar was added 3 mL of fresh anhydrous N,N-dimethylacetamide (Aldrich) under a sweep of dry nitrogen. Anhydrous naltrexone base (2.01 grams) was added with stirring. Methyl bromide gas was condensed in a lecture bottle using an ice bath and 0.5 mL was measured out as a liquid into another cold graduated cylinder. The methyl bromide was poured into the naltrexone base suspension under a slow sweep of dry nitrogen. The reaction temperature and time was set at 60° C. for eight hours. At the end of eight hours the heating was discontinued and the mixture was allowed to cool to room temperature and left stirring overnight. Acetone (15 mL) was poured into the suspension to facilitate the precipitation of soluble product. The slurry was cooled to ice bath temperature and stirred. The product was recovered by vacuum filtration and washed with additional acetone. The product was dried to a constant weight in a vacuum oven set at 60° C. The yield of the unpurified product was 1.63 g.

EXAMPLE 11

Synthesis of Naloxone Methobromide Bromomethane in DMF

To a 25 mL flask fitted with a condenser and stirring bar was added 5 mL of anhydrous N,N-dimethylforamide (Aldrich) under a sweep of dry nitrogen. Anhydrous naloxone base (4.11 grams) was added with stirring. Methyl bromide gas was condensed in a lecture bottle using an ice bath and 0.5 mL was measured out as a liquid into another cold graduated cylinder. The methyl bromide was poured into the naltrexone base suspension under a slow sweep of dry nitrogen. The reaction temperature and time was set at 60° C. for ten hours. At the end of ten hours the heating was discontinued and the mixture was allowed to cool to room temperature and left stirring over the weekend. Acetone (10 mL) was poured into the suspension to facilitate the precipitation of soluble product. The slurry was cooled to ice bath temperature with stirring. The product was recovered by vacuum filtration and washed with additional acetone. The product was dried in a vacuum oven set at 60° C. for two hours. 2.89 Grams of the crude product were recovered. Recrystallization from methanol/water (20 mL, 8:2) yielded 2.43 grams of a white crystalline product.

EXAMPLE 12

Synthesis of N-Cyclopropylmethyl-Noroxymorphone MethoChloride Methyl Chloride in DMF To a 25 mL 3-necked flask fitted with a condenser connected to a bubbler and containing a stirring bar was added 10 mL of anhydrous NN-dimethylformamide (Aldrich) under a sweep of dry nitrogen. Anhydrous naltrexone base (4.02 grams) was added with stirring. A cylinder of methyl chloride gas was connected to a dispersion tube in the solution and the nitrogen sweep was stopped. The methyl chloride was bubbled into the solution at 70° C. overnight. No detectable product was observed upon cooling. Yield, however, could be improved by addition of an iodide or bromide salt, e.g., NaI, NaBr, i.e., in-situ conversion of methyl chloride to methyl iodide or methyl bromide.

The invention claimed is:

1. A process for the preparation of a quaternary derivative of a tertiary N-substituted morphinan alkaloid, the process comprising contacting a tertiary N-substituted morphinan alkaloid substrate with an alkylating agent in an anhydrous solvent system, wherein the solvent system comprises an aprotic dipolar solvent selected from the group consisting of dimethylacetamide, dimethylformamide, 1-methyl-2-pyrrolidinone, hexamethylphosphoramide, and mixtures thereof with the aprotic dipolar solvent constituting at least 25 wt % of the solvent system, the contacting is carried out within a temperature range of about 55° C. to about 85° C., the tertiary N-substituted morphinan alkaloid substrate and the quaternary derivative correspond to Formulae 1 and Formula 1A, respectively:

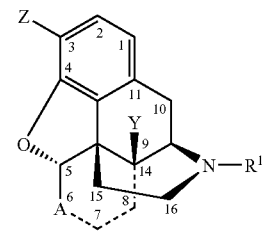

Formula 1

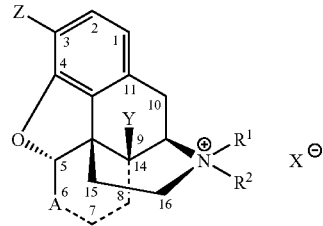

Formula 1A

A is —C(O)—, —C(S)—, —C(=CH$_2$)—, —CH(A$_1$)—, or —C(A$_1$)=,

A$_1$ is hydroxy, alkoxy, or acyloxy, each R is independently hydrocarbyl,

R$^1$ is hydrocarbyl or substituted hydrocarbyl,

R$^2$ is hydrocarbyl or substituted hydrocarbyl,

X$^\ominus$ is an anion,

Y, if present, is hydrogen, hydroxy, alkoxy, acyloxy, —OTHP, —OSiR$_3$, —OBn, —OBs, —OTs, or OMs, Z is hydroxy, alkoxy, acyloxy, —OTHP, —OSiR$_3$, —OBn, —OBs, —OTs, or —OMs, and the dashed lines between the carbon atoms at positions 6 and 7, 7 and 8, and 8 and 14, respectively, represent (i) carbon-carbon single bonds, (ii) carbon-carbon single bonds between positions 6 and 7 and between positions 8 and 14, and a double bond between positions 7 and 8, or (iii) conjugated carbon-carbon double bonds between positions 6 and 7 and positions 8 and 14, with the proviso that Y is not present if there is a double bond between the carbons at positions 8 and 14.

2. The process of claim 1 wherein the tertiary N-substituted morphinan alkaloid substrate and the quaternary derivative correspond to Formula 2 and 2A, respectively:

Formula 2

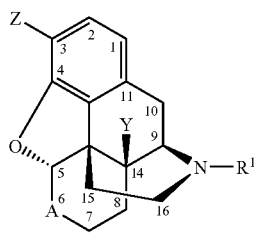

Formula 2A

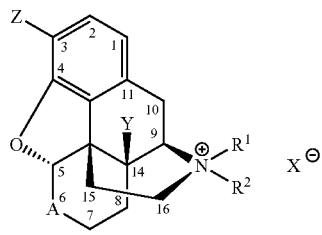

A is —C(O)—, —C(S)—, —C(=CH$_2$)—, or —CH(A$_1$)—,
A$_1$ is hydroxy, alkoxy, or acyloxy,
R$^1$ is hydrocarbyl or substituted hydrocarbyl,
R$^2$ is hydrocarbyl or substituted hydrocarbyl,
X$^\ominus$ is an anion,
Y is hydrogen, hydroxy, alkoxy, or acyloxy, and
Z is hydroxy, alkoxy, or acyloxy.

3. The process of claim 2 wherein the tertiary N-substituted morphinan alkaloid substrate is naltrexone ((5α)-17-(cyclopropylmethyl)-4,5-epoxy-3,14-dihydroxymorphinan-6-one), oxymorphone ((5α)-4,5-epoxy-3,14-dihydroxy-17-methylmorphinan-6-one), oxycodone ((5α)-4,5-epoxy-14-hydroxy-3-methoxy-17-methylmorphinan-6-one), hydromorphone ((5α)-4,5-epoxy-3-hydroxy-17-methylmorphinan-6-one), naloxone ((5α)-4,5-epoxy-3,14-dihydroxy-17-(2-propenyl)morphinan-6-one), nalmefene ((5α)-17-(cyclopropylmethyl)-4,5-epoxy-6-methylenemorphinan-3,14-diol) or nalbuphine ((5α)-17-(cyclobutylmethyl)-4,5-epoxymorphinan-3,6,14-triol).

4. The process of claim 1 wherein the alkylating agent is methyl bromide.

5. The process according to claim 1 wherein said process is carried out at a pressure of less than 1.25 atmospheres.

6. The process according to claim 1 wherein the aprotic dipolar solvent constitutes at least 75 wt. % of the solvent system.

7. The process according to claim 1 wherein said aprotic dipolar solvent is 1-methyl-2-pyrrolidinone.

8. The process according to claim 1 wherein Y and Z are independently —OCH$_3$, —OAc, —OTHP, —OSiR$_3$, —OBn, —OBz, —OBs, —OTs, or —OMs wherein each R is independently hydrocarbyl.

9. The process according to claim 1 wherein said anhydrous solvent system contains less than 0.2 wt. % water and is maintained in a moisture-free atmosphere in a reaction vessel.

10. The process according to claim 1 wherein said anhydrous solvent system contains less than 0.1 wt. % water.

11. The process according to claim 1 wherein said anhydrous solvent system contains less than 0.05 wt. % water.

12. The process according to claim 11 wherein said alkylating agent is a methylating agent.

13. The process according to claim 11 wherein said alkylating agent and said substrate are present in a mole ratio of between 1:1 and 1.5:1, respectively.

14. The process according to claim 1 wherein said anhydrous solvent system and said substrate are present in a volume-to-weight ratio of 1.5:1-1.75:1.

15. The process of claim 1 wherein the tertiary N-substituted morphinan alkaloid substrate and the quaternary derivative correspond to Formulae 3 and 3A, respectively:

Formula 3

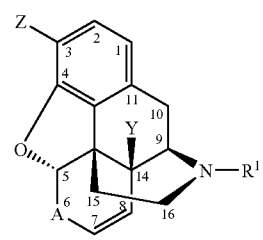

Formula 3A

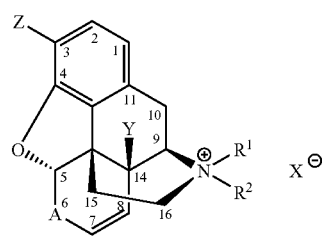

A is —C(O)—, —C(S)—, —C(=CH$_2$)—, or —CH(A$_1$)—,
A$_1$ is hydroxy, alkoxy, or acyloxy,
R$^1$ is hydrocarbyl or substituted hydrocarbyl,
R$^2$ is hydrocarbyl or substituted hydrocarbyl, and
X$^\ominus$ is an anion,
Y is hydrogen, hydroxy, alkoxy, or acyloxy, and
Z is hydroxy, alkoxy, or acyloxy.

16. The process of claim 15 wherein the tertiary N-substituted morphinan alkaloid substrate is morphine ((5α,6α)-7,8-didehydro-4,5-epoxi-17-methylmorphinan-3,6-diol), codeine ((5α,6α)-7,8-didehydro-4,5-epoxi-3-methoxy-17-methylmorphinan-6-ol), codeinone ((5α)-7,8-didehydro-4,5-epoxy-3-methoxy-17-methylmorphinan-6-one) or 14-hydroxy-codeinone ((5α)-7,8-didehydro-4,5-epoxy-14-hydroxy-3-methoxy-17-methylmorphinan-6-one).

17. The process of claim 1 wherein the tertiary N-substituted morphinan alkaloid substrate and the quaternary derivative correspond to Formulae 4 and 4A, respectively:

Formula 4

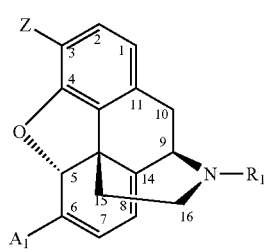

-continued

Formula 4A

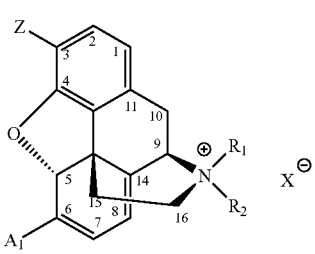

$A_1$ is hydroxy, alkoxy, or acyloxy,
$R^1$ is hydrocarbyl or substituted hydrocarbyl,
$R^2$ is hydrocarbyl or substituted hydrocarbyl,
$X^\ominus$ is an anion, and
Z is hydroxy, alkoxy, or acyloxy.

18. A process for the preparation of a quaternary derivative of a tertiary N-substituted morphinan alkaloid, the process comprising contacting a tertiary N-substituted morphinan alkaloid substrate with an alkylating agent in an anhydrous solvent system, wherein the solvent system comprises 1-methyl-2-pyrrolidinone with the 1-methyl-2-pyrrolidinone constituting at least 25 wt % of the solvent system, the tertiary N-substituted morphinan alkaloid substrate and the quaternary derivative correspond to Formulae 1 and 1A, respectively:

Formula 1

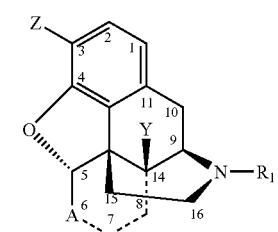

Formula 1A

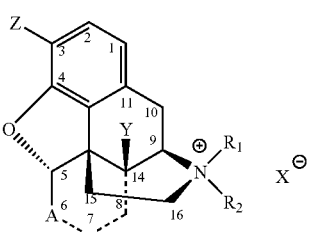

A is —C(O)—, —C(S)—, —C(=CH$_2$)—, —CH(A$_1$)—, or —C(A$_1$)=,
$A_1$ is hydroxy, alkoxy, or acyloxy,
each R is independently hydrocarbyl,
$R^1$ is hydrocarbyl or substituted hydrocarbyl,
$R^2$ is hydrocarbyl or substituted hydrocarbyl,
$X^\ominus$ is an anion,
Y, if present, is hydrogen, hydroxy, alkoxy, acyloxy, —OTHP, —OSiR$_3$, —OBn, —OBs, —OTs, or —OMs,
Z is hydroxy, alkoxy, acyloxy, —OTHP, —OSiR$_3$, —OBn, —OBs, —OTs, or —OMs, and the dashed lines between the carbon atoms at positions 6 and 7, 7 and 8, and 8 and 14, respectively, represent (i) carbon-carbon single bonds, (ii) carbon-carbon single bonds between positions 6 and 7 and between positions 8 and 14, and a double bond between positions 7 and 8, or (iii) conjugated carbon-carbon double bonds between positions 6 and 7 and positions 8 and 14, with the proviso that Y is not present if there is a double bond between the carbons at positions 8 and 14.

19. The process of claim 18 wherein the tertiary N-substituted morphinan alkaloid substrate and the quaternary derivative correspond to Formulae 2 and 2A, respectively:

Formula 2

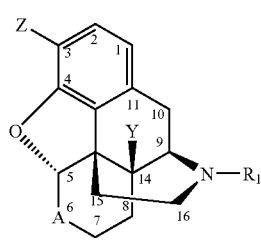

Formula 2A

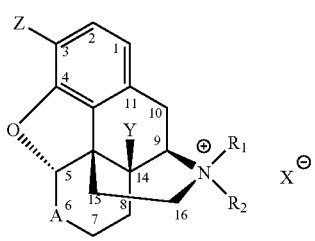

A is —C(O)—, —C(S)—, —C(=CH$_2$)—, or —CH(A$_1$)—,
$A_1$ is hydroxy, alkoxy, or acyloxy,
$R^1$ is hydrocarbyl or substituted hydrocarbyl,
$R^2$ is hydrocarbyl or substituted hydrocarbyl,
$X^\ominus$ is an anion,
Y is hydrogen, hydroxy, alkoxy, or acyloxy, and
Z is hydroxy, alkoxy, or acyloxy.

20. The process of claim 19 wherein the tertiary N-substituted morphinan alkaloid substrate is naltrexone ((5α)-17-(cyclopropylmethyl)-4,5-epoxy-3,14-dihydroxymorphinan-6-one), oxymorphone ((5α)-4,5-epoxy-3,14-dihydroxy-17-methylmorphinan-6-one), oxycodone ((5α)-4,5-epoxy-14-hydroxy-3-methoxy-17-methylmorphinan-6-one), hydromorphone ((5α)-4,5-epoxy-3-hydroxy-17-methylmorphinan-6-one), naloxone ((5α)-4,5-epoxy-3,14-dihydroxy-17-(2-propenyl)morphinan-6-one), nalmefene ((5α)-17-(cyclopropylmethyl)-4,5-epoxy-6-methylenemorphinan-3,14-diol) or nalbuphine ((5α)-17-(cyclobutylmethyl)-4,5-epoxymorphinan-3,6,14-triol).

21. The process of claim 18 wherein the alkylating agent is methyl bromide.

22. The process according to claim 18 wherein said process is carried out at a pressure of less than 1.25 atmospheres.

23. The process according to claim 18 wherein the 1-methyl-2-pyrrolidinone constitutes at least 75 wt. % of the solvent system.

24. The process according to claim 18 wherein Y and Z are independently —OCH3, —OAc, —OTHP, —OSiR$_3$, —OBn, —OBz, —OBs, —OTs, or —OMs wherein each R is independently hydrocarbyl.

25. The process according to claim 18 wherein said anhydrous solvent system contains less than 0.2 wt. % water and is maintained in a moisture-free atmosphere in a reaction vessel.

26. The process according to claim 18 wherein said anhydrous solvent system contains less than 0.1 wt. % water.

27. The process according to claim 18 wherein said anhydrous solvent system contains less than 0.05 wt. % water.

28. The process according to claim 27 wherein said alkylating agent is a methylating agent.

29. The process according to claim 27 wherein said alkylating agent and said substrate are present in a mole ratio of between 1:1 and 1.5:1, respectively.

30. The process according to claim 18 wherein said 1-methyl-2-pyrrolidinone and said substrate are present in a volume-to-weight ratio of 1.5:1-1.75:1.

31. The process according to claim 18 wherein said contacting is carried out within a temperature range of about 55° C. to about 85° C.

32. The process of claim 18 wherein the tertiary N-substituted morphinan alkaloid substrate and the quaternary derivative correspond to Formulae 3 and 3A, respectively:

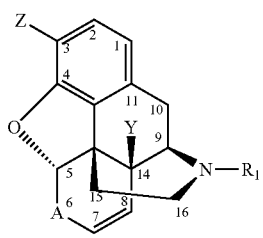

Formula 3

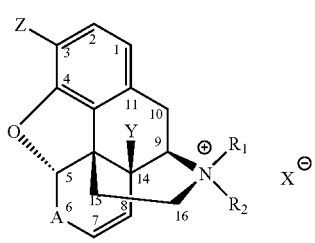

Formula 3A

A is —C(O)—, —C(S)—, —C(=CH$_2$)—, or —CH(A$_1$)—,

A$_1$ is hydroxy, alkoxy, or acyloxy,

R$^1$ is hydrocarbyl or substituted hydrocarbyl,

R$^2$ is hydrocarbyl or substituted hydrocarbyl,

X$^\ominus$ is an anion,

Y is hydrogen, hydroxy, alkoxy, or acyloxy, and

Z is hydroxy, alkoxy, or acyloxy.

33. The process of claim 32 wherein the tertiary N-substituted morphinan alkaloid substrate is morphine ((5α,6α)-7,8-didehydro-4,5-epoxi-17-methylmorphinan-3,6-diol), codeine ((5α,6α)-7,8-didehydro-4,5-epoxi-3-methoxy-17-methylmorphinan-6-ol), codeinone ((5α)-7,8-didehydro-4,5-epoxy-3-methoxy-17-methylmorphinan-6-one) or 14-hydroxy-codeinone ((5α)-7,8-didehydro-4,5-epoxy-14-hydroxy-3-methoxy-17-methylmorphinan-6-one).

34. The process of claim 18 wherein the tertiary N-substituted morphinan alkaloid substrate and the quaternary derivative correspond to Formulae 4 and 4A, respectively:

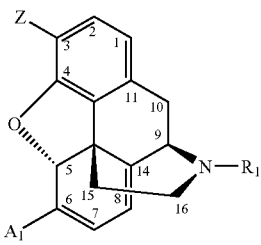

Formula 4

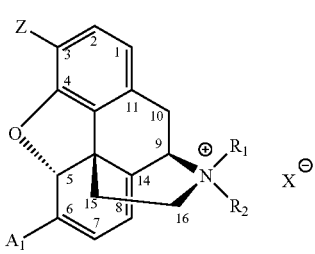

Formula 4A

A$_1$ is hydroxy, alkoxy, or acyloxy,

R$^1$ is hydrocarbyl or substituted hydrocarbyl,

R$^2$ is hydrocarbyl or substituted hydrocarbyl,

X$^\ominus$ is an anion, and

Z is hydroxy, alkoxy, or acyloxy.

35. A process for the preparation of a quaternary derivative of a tertiary N-substituted morphinan alkaloid, the process comprising contacting a tertiary N-substituted morphinan alkaloid substrate with methyl bromide in an anhydrous solvent system, wherein the solvent system comprises an aprotic dipolar solvent selected from the group consisting of dimethylacetamide, dimethylformamide, 1-methyl-2-pyrrolidinone, hexamethylphosphoramide, and mixtures thereof with the aprotic dipolar solvent constituting at least 25 wt % of the solvent system, the tertiary N-substituted morphinan alkaloid substrate and the quaternary derivative have the structures of Formulae 1 and 1A, respectively:

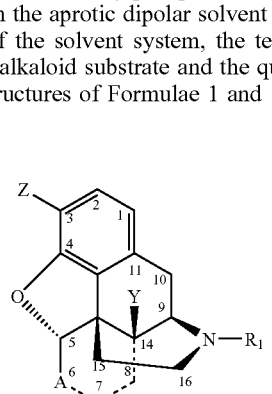

Formula 1

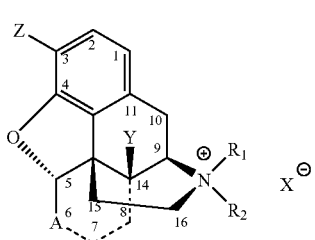

Formula 1A

A is —C(O)—, —C(S)—, —C(=CH$_2$)—, —CH(A$_1$)—, or —C(A$_1$)=,

A$_1$ is hydroxy, alkoxy, or acyloxy, each R is independently hydrocarbyl,
$R^1$ is hydrocarbyl or substituted hydrocarbyl,
$R^2$ is hydrocarbyl or substituted hydrocarbyl,
$X^⊖$ is an anion,
Y, if present, is hydrogen, hydroxy, alkoxy, acyloxy, —OTHP, —OSiR$_3$, —OBn, —OBs, —OTs, or —OMs,
Z is hydroxy, alkoxy, acyloxy, —OTHP, —OSiR$_3$, —OBn, —OBs, —OTs, or —OMs, and the dashed lines between the carbon atoms at positions 6 and 7, 7 and 8, and 8 and 14, respectively, represent (i) carbon-carbon single bonds, (ii) carbon-carbon single bonds between positions 6 and 7 and between positions 8 and 14, and a double bond between positions 7 and 8, or (iii) conjugated carbon-carbon double bonds between positions 6 and 7 and positions 8 and 14, with the proviso that Y is not present if there is a double bond between the carbons at positions 8 and 14.

36. The process of claim 35 wherein the tertiary N-substituted morphinan alkaloid substrate and the quaternary derivative correspond to Formulae 2 and 2A, respectively:

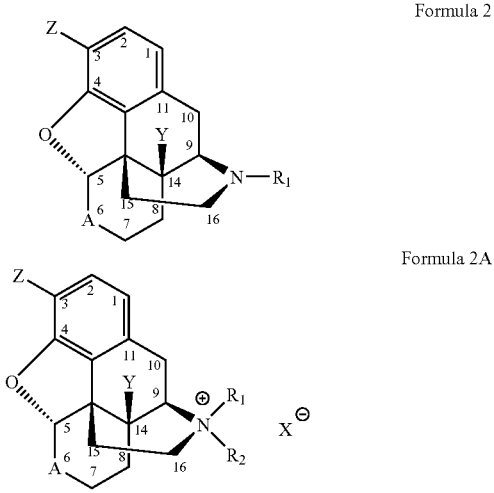

Formula 2

Formula 2A

A is —C(O)—, —C(S)—, —C(=CH$_2$)—, or —CH(A$_1$)—,
A$_1$ is hydroxy, alkoxy, or acyloxy,
$R^1$ is hydrocarbyl or substituted hydrocarbyl,
$R^2$ is hydrocarbyl or substituted hydrocarbyl,
$X^⊖$ is an anion,
Y is hydrogen, hydroxy, alkoxy, or acyloxy, and
Z is hydroxy, alkoxy, or acyloxy.

37. The process of claim 36 wherein the tertiary N-substituted morphinan alkaloid substrate is naltrexone ((5α)-17-(cyclopropylmethyl)-4,5-epoxy-3,14-dihydroxymorphinan-6-one), oxymorphone ((5α)-4,5-epoxy-3,14-dihydroxy-17-methylmorphinan-6-one), oxycodone ((5α)-4,5-epoxy-14-hydroxy-3-methoxy-17-methylmorphinan-6-one), hydromorphone ((5α)-4,5-epoxy-3-hydroxy-17-methylmorphinan-6-one), naloxone ((5α)-4,5-epoxy-3,14-dihydroxy-17-(2-propenyl)morphinan-6-one), nalmefene ((5α)-17-(cyclopropylmethyl)-4,5-epoxy-6-methylenemorphinan-3,14-diol) or nalbuphine ((5α)-17-(cyclobutylmethyl)-4,5-epoxymorphinan-3,6,14-triol).

38. The process according to claim 35 wherein said process is carried out at a pressure of less than 1.25 atmospheres.

39. The process according to claim 35 wherein the aprotic dipolar solvent constitutes at least 75 wt. % of the solvent system.

40. The process according to claim 35 wherein said aprotic dipolar solvent is 1-methyl-2-pyrrolidinone.

41. The process according to claim 35 wherein Y and Z are independently —OCH$_3$, —OAc, —OTHP, —OSiR$_3$, —OBn, —OBz, —OBs, —OTs, or —OMs wherein each R is independently hydrocarbyl.

42. The process according to claim 35 wherein said anhydrous solvent system contains less than 0.2 wt. % water and is maintained in a moisture-free atmosphere in a reaction vessel.

43. The process according to claim 35 wherein said anhydrous solvent system contains less than 0.1 wt. % water.

44. The process according to claim 35 wherein said anhydrous solvent system contains less than 0.05 wt. % water.

45. The process according to claim 44 wherein said methyl bromide and said substrate are present in a mole ratio of between 1:1 and 1.5:1, respectively.

46. The process according to claim 35 wherein said anhydrous solvent system and said substrate are present in a volume-to-weight ratio of 1.5:1-1.75:1.

47. The process according to claim 35 wherein said contacting is carried out within a temperature range of about 55° C. to about 85° C.

48. The process of claim 35 wherein the tertiary N-substituted morphinan alkaloid substrate and the quaternary derivative correspond to Formulae 3 and 3A, respectively:

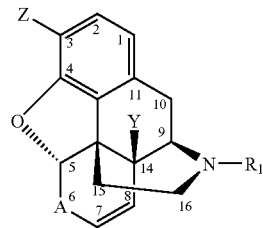

Formula 3

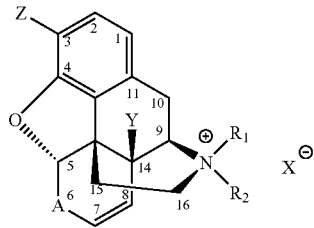

Formula 3A

A is —C(O)—, —C(S)—, —C(=CH$_2$)—, or —CH(A$_1$)—,
A$_1$ is hydroxy, alkoxy, or acyloxy,
$R^1$ is hydrocarbyl or substituted hydrocarbyl,
$R^2$ is hydrocarbyl or substituted hydrocarbyl,
$X^⊖$ is an anion,
Y is hydrogen, hydroxy, alkoxy, or acyloxy, and
Z is hydroxy, alkoxy, or acyloxy.

49. The process of claim 48 wherein the tertiary N-substituted morphinan alkaloid substrate is morphine ((5α,6α)-7,8-didehydro-4,5-epoxi-17-methylmorphinan-3,6-diol), codeine ((5α,6α)-7,8-didehydro-4,5-epoxi-3-methoxy-17-methylmorphinan-6-ol), codeinone ((5α)-7,8-didehydro-4,5-epoxy-3-methoxy-17-methylmorphinan-6-one) or 14-hydroxy-codeinone ((5α)-7,8-didehydro-4,5-epoxy-14-hydroxy-3-methoxy-17-methylmorphinan-6-one).

50. The process of claim 35 wherein the tertiary N-substituted morphinan alkaloid substrate and the quaternary derivative correspond to Formulae 4 and 4A, respectively:

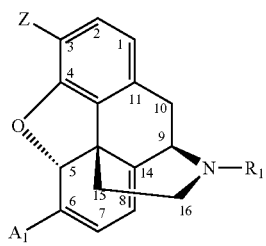

Formula 4

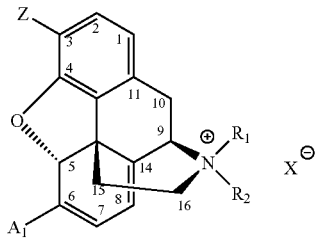

Formula 4A $A_1$ is hydroxy, alkoxy, or acyloxy,
$R^1$ is hydrocarbyl or substituted hydrocarbyl,
$R^2$ is hydrocarbyl or substituted hydrocarbyl,
$X^\ominus$ is an anion, and
Z is hydroxy, alkoxy, or acyloxy.

* * * * *